Jan. 4, 1944. R. ENGLE Plant Pat. 612
CARNATION PLANT
Filed June 21, 1943
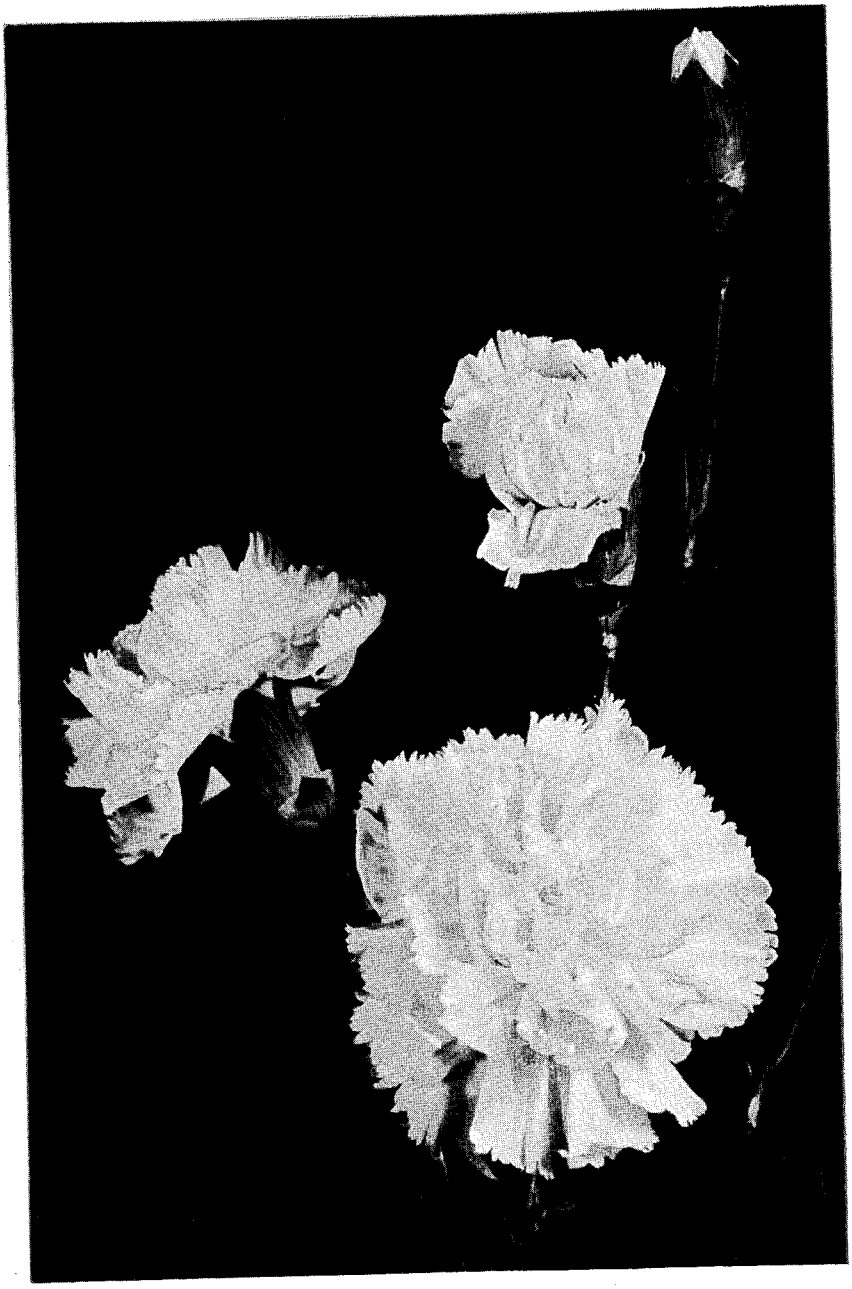
INVENTOR
Russell Engle
By Orville M. Kile
Plant Pat. Agt.

Patented Jan. 4, 1944

Plant Pat. 612

UNITED STATES PATENT OFFICE

612

CARNATION PLANT

Russell Engle, Kokomo, Ind., assignor to Tom Knipe, Florist, Kokomo, Ind., a partnership of Indiana Application June 21, 1943, Serial No. 491,705

1 Claim. (Cl. 47—60)

My present invention relates to improvements in white carnations usually known as greenhouse forcing varieties, and resulted from definite breeding efforts.

The new variety resulted from a cross between Myra as the male parent and an unnamed white seedling as the female parent.

One of the outstanding features of this new variety is its exceedingly free branching habit when topped. When permitted to grow and produce bloom, these branches will have new growth started at the base or lower nodes of the stem. This growth is from 4 to 6 inches long when the flower blooms. Since it would take 6 to 8 weeks to produce this amount of growth, it means that new blooms could be produced 6 to 8 weeks earlier than with varieties which do not have this branching habit or which do not start the branching growth until after the bloom is cut.

Another outstanding feature is the consistently large size and heavy substance of its blossoms. It is an especially strong and vigorous grower and prolific producer of flowers. The calyx of its blossom is exceedingly strong and tough and seldom splits, even with the large heavy blossom which is consistently produced. The plant is particularly disease resistant; and it is not easily injured by insecticides and fungicides.

Asexual reproduction of my new variety has proved its qualities to be firmly fixed.

The accompanying illustration which is a part of this specification, shows three specimens of this variety in various stages of opening. The following description is based on flowers obtained early in April. Color plate references indicate Ridgway's Color Standards and Nomenclature.

*The plant*

Growth habit: Has very strong root growth from cuttings, and ordinarily grows to a height of 3 to 3½ feet. Is very free-branching and produces much side growth while blooming, as well as afterward. This side growth during blooming enables the grower to obtain blooms on new plants much earlier than would otherwise be possible.

Blooming habit: Continuous; prolific.

Stems: Long and amply strong to hold large blossom erect. Color approximately Empire Green (Pl. XXXII). *Internodes*—about 3½ to 4 inches long.

Foliage: Abundant; approximately Dark Dull Yellow Green (Pl. XXXII), covered with gray bloom. New foliage of sideshoots is approximately Forest Green (Pl. XXII). Leaves are curled and average 4½ to 5 inches long and ⅜ inch wide.

Disease resistance: Very resistant to diseases common to carnations.

*The flower*

Bud: Medium in size. The unopened bud is rather blunt, becoming more tapered as it develops.

Blossom:

*Form.*—Full and high-centered. Never appears lacking in fullness.

*Size.*—Very large. Averages 3½ inches in diameter but frequently grows four inches in diameter.

*Petalage.*—Usual petalage is 45 to 50 petals.

*Color.*—Pure white throughout.

*Petals.*—Texture—very substantial. Size—2½ inches long, including shank which is about half the length; outer petals average 1½ inches wide. Edge—irregularly serrated and notched.

*Fragrance.*—Strong cinnamon fragrance.

Keeping quality: As a cut flower, keeps better than any other white carnation variety known to me.

Reproductive organs:

*Ovary.*—Medium in size; approximately ⅜ inch high.

*Pistils.*—Two, sometimes three. White; curled at tip; average length 1¾ inches.

*Stamens.*—Few; white; average length 1¼ inches.

*Comparison*

The variety that most resembles my new variety is Stardust, the subject of Plant Patent No. 491, but the two varieties differ principally as follows:

1. Difference of parentage.

2. My new variety develops greater sidegrowth before blossoms develop, thus allowing new plants from sidegrowth to develop blossoms much earlier than would be possible with varieties which develop less sidegrowth while blooming, such as Stardust.

3. Root growth is stronger and more active in my new variety.

4. Internodes of my variety are shorter, thus making more foliage possible.

5. Opening of buds of my new variety is the usual type, while Stardust opens in the peculiar pinwheel fashion described in the patent.

6. Grown under similar conditions, flowers of my new variety are consistently larger.

7. Flowers of my new variety have greater petalage.

8. Serrations of the petals of flowers of my new variety are somewhat deeper than in the petals of Stardust.

9. Although the general description of the form of the flower is similar, the two varieties differ somewhat in flower appearance, due partly to the arrangement of the petals of Stardust which shows more of their flat surface than in the flowers of my new variety.

10. The calyx of my new variety splits less often, due probably to the expansion provided by the deeper puffs at the top of each lobe of the calyx.

Having thus disclosed my invention, I claim:

The new and useful variety of carnation plant herein shown and described, characterized particularly by its strong and active root growth; its extensive development of sidegrowth while in bloom; its disease resistance; its consistently large flowers of heavy substance, pure white color, intense fragrance, and strong calyx which seldom splits; and its exceptionally good keeping quality as a cut flower.

RUSSELL ENGLE.